US011786761B2

(12) United States Patent
Kirk et al.

(10) Patent No.: US 11,786,761 B2
(45) Date of Patent: Oct. 17, 2023

(54) ULTRASONIC ROBOTIC TOOL ACTUATION

(71) Applicant: Cilag GmbH International, Zug (CH)

(72) Inventors: Jeffery Kirk, Liberty Township, OH (US); Kevin D. Felder, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 749 days.

(21) Appl. No.: 16/669,996

(22) Filed: Oct. 31, 2019

(65) Prior Publication Data
US 2020/0078611 A1 Mar. 12, 2020

Related U.S. Application Data

(62) Division of application No. 15/386,516, filed on Dec. 21, 2016.

(51) Int. Cl.
*A61B 34/35* (2016.01)
*A61B 17/32* (2006.01)
(Continued)

(52) U.S. Cl.
CPC ........ *A61N 7/02* (2013.01); *A61B 17/320092* (2013.01); *A61B 34/30* (2016.02);
(Continued)

(58) Field of Classification Search
CPC .... A61B 17/320092; A61B 2017/2912; A61B 2017/2924; A61B 2017/320094;
(Continued)

(56) References Cited

U.S. PATENT DOCUMENTS 5,582,617 A * 12/1996 Klieman ................ A61B 34/71
606/174
8,114,345 B2 2/2012 Dlugos, Jr. et al.
(Continued)

FOREIGN PATENT DOCUMENTS

| EP | 2727545 A1 | 5/2014 |
| EP | 3097874 A1 | 11/2016 |
| WO | WO-2007014215 A2 | 2/2007 |

OTHER PUBLICATIONS

International Search Report and Written Opinion for International App. No. PCT/IB2017/057703 dated Mar. 5, 2018 (13 pages).

*Primary Examiner* — Martin T Ton
(74) *Attorney, Agent, or Firm* — Mintz Levin Cohn Ferris Glovsky and Popeo, P.C.

(57) ABSTRACT

Described herein include various embodiments of a tool assembly for performing endoscopic surgery that can be used manually and/or with a robotic surgical system. The tool assembly can include a shaft assembly that extends from a housing of the tool assembly. A distal end of the shaft can include an end effector that includes a clamp arm pivotally coupled to a blade for cutting and/or sealing tissue. Pivoting of the clamp arm between the open and closed configurations can be caused by movement of a yoke that is slidably disposed within the housing of the tool assembly. For example, the yoke can be caused to move by one or more outputs (e.g., a manual output, a rotary output, and/or a linear mechanical output). Furthermore, some tool assembly embodiments can include a biasing system that biases the yoke such that the clamp arm is in the open configuration. In some embodiments, the tool assembly can be configured for tissue spread dissection using the clamp arm and blade.

9 Claims, 13 Drawing Sheets

(51) Int. Cl.
*A61B 34/00* (2016.01)
*A61N 7/02* (2006.01)
*A61B 34/30* (2016.01)
*A61B 18/00* (2006.01)
*A61B 17/00* (2006.01)
*A61B 17/29* (2006.01)

(52) U.S. Cl.
CPC .............. *A61B 34/35* (2016.02); *A61B 34/70* (2016.02); *A61B 2017/0046* (2013.01); *A61B 2017/00402* (2013.01); *A61B 2017/00477* (2013.01); *A61B 2017/2912* (2013.01); *A61B 2017/320094* (2017.08); *A61B 2017/320095* (2017.08); *A61B 2018/0063* (2013.01); *A61B 2018/00601* (2013.01); *A61B 2034/305* (2016.02)

(58) Field of Classification Search
CPC . A61B 2017/3201; A61B 34/30; A61B 34/35; A61B 34/70; A61B 2017/00371; A61B 2017/00389; A61B 2017/00393; A61B 2017/29; A61B 2017/32; A61B 2017/2943; A61B 2017/2938; A61B 2017/2919; A61B 2017/320093; A61B 18/1447
See application file for complete search history.

(56) References Cited

U.S. PATENT DOCUMENTS

| | | |
|---|---|---|
| 9,510,895 B2 | 12/2016 | Houser et al. |
| 10,143,524 B2 | 12/2018 | Koch et al. |
| 10,471,282 B2 | 11/2019 | Kirk |
| 11,382,704 B2* | 7/2022 | Overmyer ............... A61B 34/30 |
| 2002/0072766 A1 | 6/2002 | Hunt et al. |
| 2003/0083683 A1 | 5/2003 | Schwemberger et al. |
| 2006/0079874 A1 | 4/2006 | Faller et al. |
| 2006/0079879 A1 | 4/2006 | Faller et al. |
| 2011/0087220 A1 | 4/2011 | Felder et al. |
| 2014/0005678 A1 | 1/2014 | Shelton, IV et al. |
| 2014/0005704 A1 | 1/2014 | Vakharia et al. |
| 2014/0276723 A1 | 9/2014 | Parihar et al. |
| 2014/0276738 A1* | 9/2014 | Price .................. A61B 18/1445 606/33 |
| 2014/0276931 A1 | 9/2014 | Parihar et al. |
| 2014/0305991 A1 | 10/2014 | Parihar et al. |
| 2015/0148831 A1* | 5/2015 | Faller ................. A61B 17/2909 606/169 |
| 2015/0173840 A1 | 6/2015 | Lohmeier |
| 2015/0209059 A1* | 7/2015 | Trees ................. A61B 18/1445 606/205 |
| 2015/0245850 A1* | 9/2015 | Hibner ............... A61B 18/1482 606/171 |
| 2015/0265355 A1* | 9/2015 | Prestel .................. A61B 34/30 606/130 |
| 2016/0135869 A1 | 5/2016 | Jadhav |
| 2018/0168760 A1 | 6/2018 | Koch, Jr. et al. |

* cited by examiner

ULTRASONIC ROBOTIC TOOL ACTUATION

CROSS-REFERENCE TO RELATED APPLICATIONS

This application is a divisional application of U.S. patent application Ser. No. 15/386,516 filed on Dec. 21, 2016, entitled "Ultrasonic Robotic Tool Actuation," which is hereby incorporated by reference herein in its entirety.

FIELD OF THE INVENTION

The present disclosure relates generally to methods, systems, and devices for controlling the pivoting of a clamp arm of an end effector of a surgical tool.

BACKGROUND OF THE INVENTION

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Some endoscopic surgeries require a surgical tool having an end effector positioned at a distal end of an elongate shaft that can perform functions, such as assist with grasping tissue, cutting tissue, sealing tissue, and/or releasing tissue. Such functions can require at least one input from a mechanical driving source (e.g., tool driver) to activate mechanisms within the surgical tool. These mechanisms and inputs can add unwanted complexity, size, weight, and cost to endoscopic surgery tools.

SUMMARY OF THE INVENTION

Methods, systems, and devices are provided for pivoting a clamp arm of an end effector of a surgical tool. In one embodiment, a surgical tool is provided and can include a housing and a shaft assembly that extends through the housing and distally from the housing. The shaft assembly can include a distal end with a blade and a clamp arm pivotally coupled relative to the blade. The surgical tool can also include a yoke disposed within the housing and slidably disposed around the shaft assembly. The yoke can be operatively coupled between a first actuator projecting from the housing and the clamp arm such that movement of the first actuator causes longitudinal translation of the yoke along the shaft assembly to thereby move the clamp arm between the open and closed positions. The surgical tool can also include an ultrasonic transducer disposed within the housing and coupled to the blade for delivering ultrasonic energy to the blade.

In one embodiment, the surgical tool can include at least one spring disposed within the housing and biasing the yoke distally to bias the clamp arm to the open position. The spring can be configured to compress when the yoke is moved proximally within the housing to move the clamp arm to the closed position. In certain aspects, the surgical tool can include first and second springs disposed within the housing. The second spring can be configured to compress subsequent to compression of the first spring as a result of movement of the yoke in the proximal direction. The clamp arm can be configured to apply a first force against tissue engaged between the clamp arm and the blade during a first range of motion of the yoke, and the clamp arm can be configured to apply a second force against tissue engaged between the clamp arm and the blade during a second range of motion of the yoke.

In another embodiment, the first actuator can be configured to linearly translate to cause longitudinal translation of the yoke in a first direction. The surgical tool can include a second actuator configured to linearly translate to cause longitudinal translation of the yoke in a second direction, the second direction being in a direction opposite from the first direction.

In other embodiments, the first actuator can be configured to rotate to cause longitudinal translation of the yoke. Rotation of the first actuator can cause a lead screw disposed within the housing to rotate, and rotation of the lead screw can cause longitudinal translation of the yoke. In certain embodiments, the yoke can be operatively coupled to the first actuator by a pulley assembly, a lever, or a pinion gear. The first actuator can be configured to move a first distance thereby causing the yoke to move a second distance, and the first distance can be greater than the second distance. In certain exemplary embodiments, the first actuator can include at least one protrusion formed on the yoke and extending through an opening in the housing. The housing can be configured to couple to a driver of a robotic arm of a robotic surgical system.

Surgical methods are also provided, and in one embodiment the method includes actuating a motor on a driver tool of a surgical robot to cause the motor to apply a force to an actuator on a surgical tool. Movement of the actuator can cause a yoke disposed within a housing of the surgical tool to translate linearly about a shaft assembly extending through the housing. Translation of the yoke can cause a clamp arm on an end effector of the surgical tool to move from an open position to a closed position to thereby engage tissue between the clamp arm and a blade.

In certain embodiments, proximal translation of the yoke can compress a biasing member that biases the yoke distally. In other aspects, the motor can apply one of a linear force and a rotational force to the actuator to cause the yoke to translate linearly. Movement of the yoke a first distance can cause the clamp arm to apply a first force against the tissue engaged between the clamp arm and the blade, and further movement of the yoke a second distance can cause the clamp arm to apply a second force against the tissue engaged between the clamp arm and the blade with the second force being greater than the first force.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
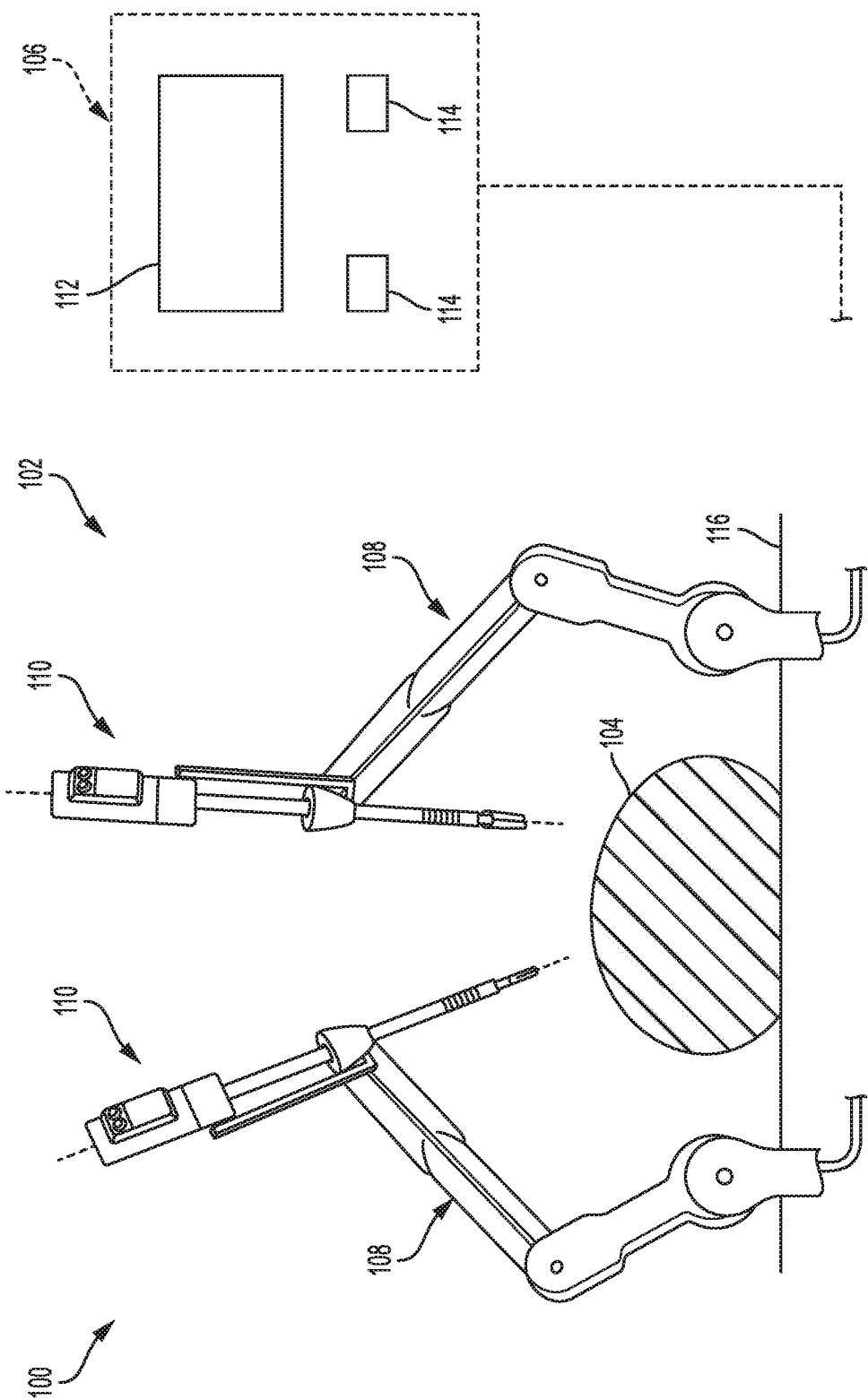
FIG. 1 is a perspective view of one embodiment of a surgical robotic system that includes a patient-side portion and a user-side portion.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In general, various embodiments of a tool assembly are provided for performing endoscopic surgery that can be used manually and/or with a robotic surgical system. The tool assembly can include a shaft assembly that extends within and distally from a housing of the tool assembly. A distal end of the shaft can include an end effector having a clamp arm pivotally coupled to a blade. For example, such an arrangement of the end effector can be used for cutting and/or sealing tissue during a surgical procedure. In order to cut or seal tissue, the clamp arm can be in an open configuration to allow tissue to be positioned between the clamp arm and the blade. The clamp arm can be caused to pivot to a closed configuration thereby compressing tissue between the clamp arm and blade to assist the blade with cutting and/or sealing the tissue, including ultrasonically. Such pivoting by the clamp arm between the open and closed configurations can be caused by movement of a yoke that is slidably disposed within the housing of the tool assembly. In some tool assembly embodiments described herein, the yoke is caused to move by one or more actuators or inputs (e.g., manual input, rotary and/or linear mechanical input) thereby causing the clamp arm to pivot to either an open configuration or a closed configuration. Furthermore, some tool assembly embodiments described herein include a biasing system within the housing that biases the yoke such that the clamp arm is biased to an open configuration, thereby only requiring a mechanical or manual output to apply a force to pivot the clamp arm into the closed configuration. In some embodiments, the tool assembly can be configured for tissue spread dissection, such as by using the clamp arm and blade to apply a great enough force against surrounding tissue to spread tissue during a surgical procedure.

As indicated above, in one embodiment the systems, devices, and methods disclosed herein can be implemented using a robotic surgical system. As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

FIG. 1 is a perspective view of one embodiment of a surgical robotic system 100 that includes a patient-side portion 102 that is positioned adjacent to a patient 104, and a user-side portion 106 that is located a distance from the patient, either in the same room and/or in a remote location. The patient-side portion 102 generally includes one or more robotic arms 108 and one or more tool assemblies 110 that are configured to releasably couple to a robotic arm 108. The user-side portion 106 generally includes a vision system 112 for viewing the patient and/or surgical site, and a control system 114 for controlling the movement of the robotic arms 108 and each tool assembly 110 during a surgical procedure.

The control system 114 can have a variety of configurations and it can be located adjacent to the patient, e.g., in the operating room, remote from the patient, e.g., in a separate control room, or it can be distributed at two or more locations. For example, a dedicated system control console can be located in the operating room, and a separate console can be located in a remote location. The control system 114 can include components that enable a user to view a surgical site of a patient being operated on by the patient-side portion 102 and/or to control one or more parts of the patient-side portion 102 (e.g., to perform a surgical procedure at the surgical site). In some embodiments, the control system 114 can also include one or more manually-operated user input devices, such as a joystick, exoskeletal glove, a powered and gravity-compensated manipulator, or the like. These user input devices can control tele-operated motors which, in turn, control the movement of the surgical system, including the robotic arms 108 and tool assemblies 110.

The patient-side portion 102 can also have a variety of configurations. As depicted in FIG. 1, the patient-side portion 102 can couple to an operating table 116. However, in some embodiments, the patient-side portion 102 can be mounted to a wall, to the ceiling, to the floor, or to other operating room equipment. Further, while the patient-side portion 102 is shown as including two robotic arms 108, more or fewer robotic arms 108 may be included. Furthermore, the patient-side portion 102 can include separate robotic arms 108 mounted in various positions, such as relative to the surgical table T (as shown in FIG. 1). Alternatively, the patient-side portion 102 can include a single assembly that includes one or more robotic arms 108 extending therefrom.

Figure 2:
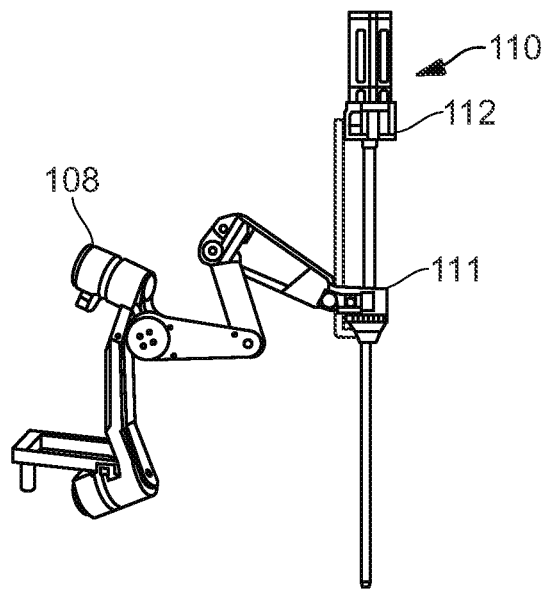
FIG. 2 is a side perspective view of a robotic arm of the surgical robotic system of FIG. 1 with a tool assembly slidably engaged with a tool driver of the robotic arm.

FIG. 2 illustrates the robotic arm 108 and tool assembly 110 releasably coupled to the robotic arm 108 in more detail. The robotic arm 108 can support and move the associated tool assembly 110 along one or more mechanical degrees of freedom (e.g., all six Cartesian degrees of freedom, five or fewer Cartesian degrees of freedom, etc.).

The robotic arm 108 can include a tool driver 112 at a distal end of the robotic arm 108, which can assist with controlling features associated with the tool assembly 110. While not shown, the tool driver 112 can include one or more motors with shafts that either rotate or translate, and that couple to the tool assembly to effect motion of various components of the tool assembly. The robotic arm 108 can also include an entry guide (e.g., a cannula mount or cannula 111) that can be a part of or removably coupled to the robotic arm 108, as shown in FIG. 2. A shaft of the tool assembly 110 can be inserted through the driver 112 and the cannula for insertion into a patient. A person skilled in the art will appreciate that the configuration of the robotic arm can vary, and that the tool assemblies disclosed herein can be used with any robotic arm.

Figure 3:
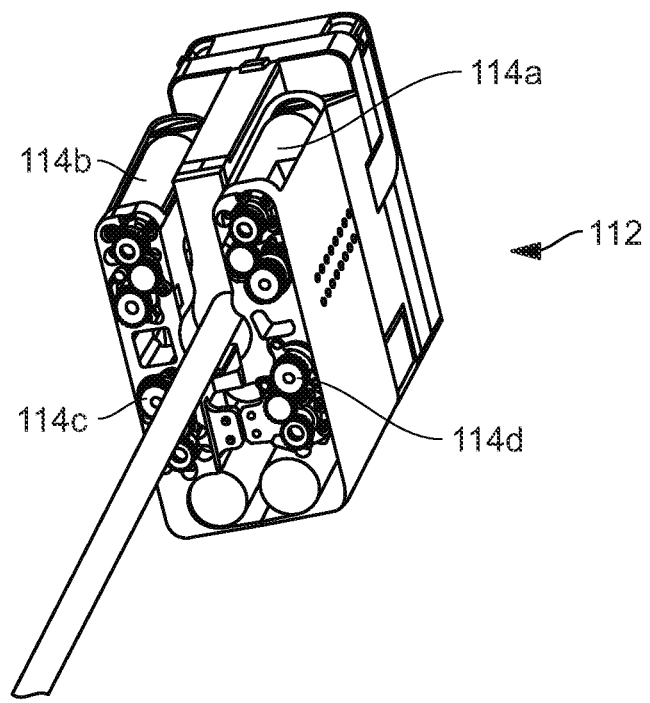
FIG. 3 is a perspective view of the tool driver of the robotic arm of FIG. 2.

FIG. 3 illustrates the tool driver 112 in more detail. As shown, the tool driver 112 can include one or more motors, e.g., four motors 114a-114d are shown, that control a variety of movements and actions associated with the tool assembly 110, as will be described in greater detail below. For example, any of the motors 114a-114d can be associated with a mechanical rotary output or a mechanical linear output, either of which can be configured to couple to a rotary input coupling or a linear input coupling associated with the tool assembly for actuating at least one mechanism of the tool assembly. The tool driver 112 can also include a shaft-receiving channel 116 formed in a sidewall thereof for receiving the shaft of the tool assembly 110. In other embodiments, the shaft can extend through on opening in the tool driver 112, or the two components can mate in various other configurations.

Figure 4A:
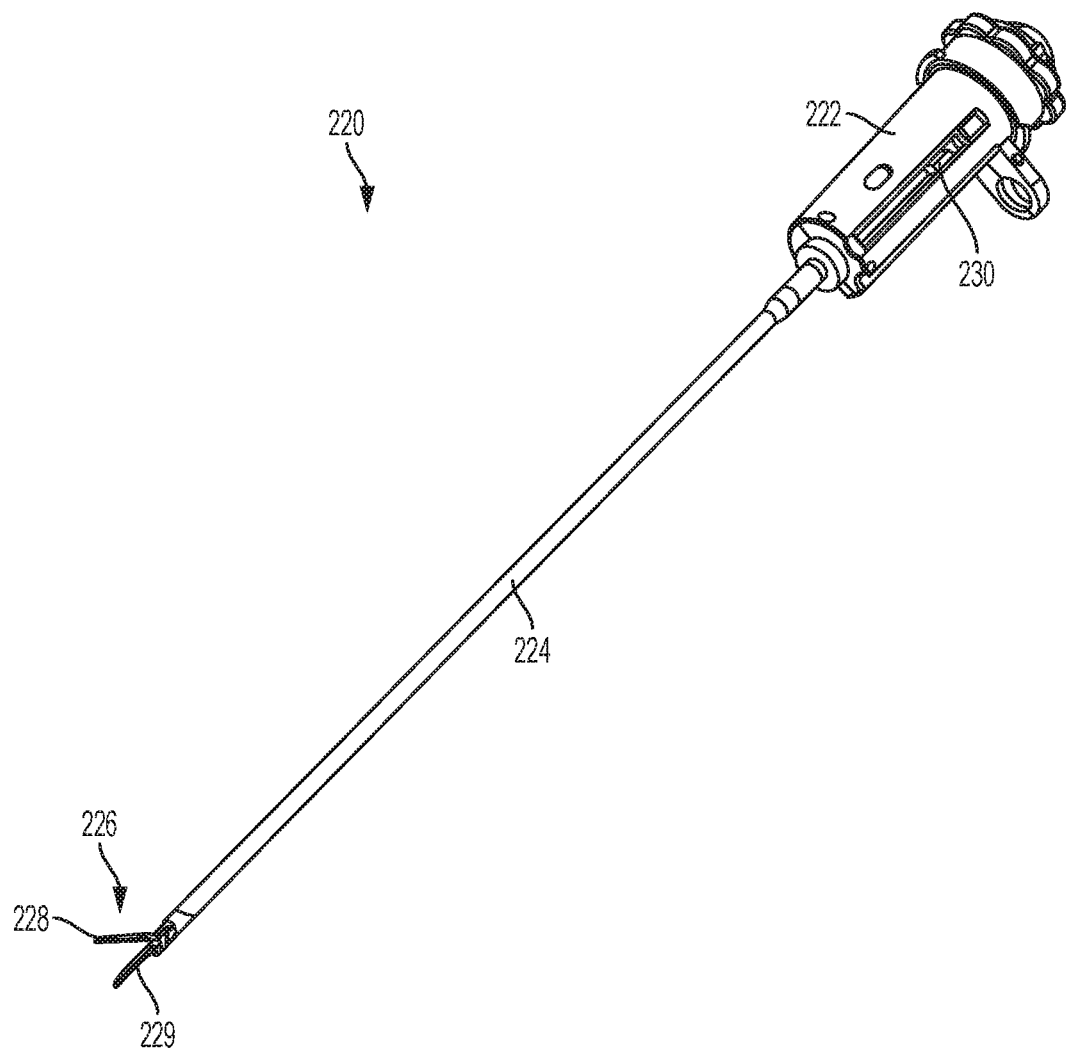
FIG. 4A is a side perspective view of one exemplary embodiment of a tool assembly having an elongate shaft extending from a housing and an end effector at a distal end of the elongate shaft.
Figure 4B:
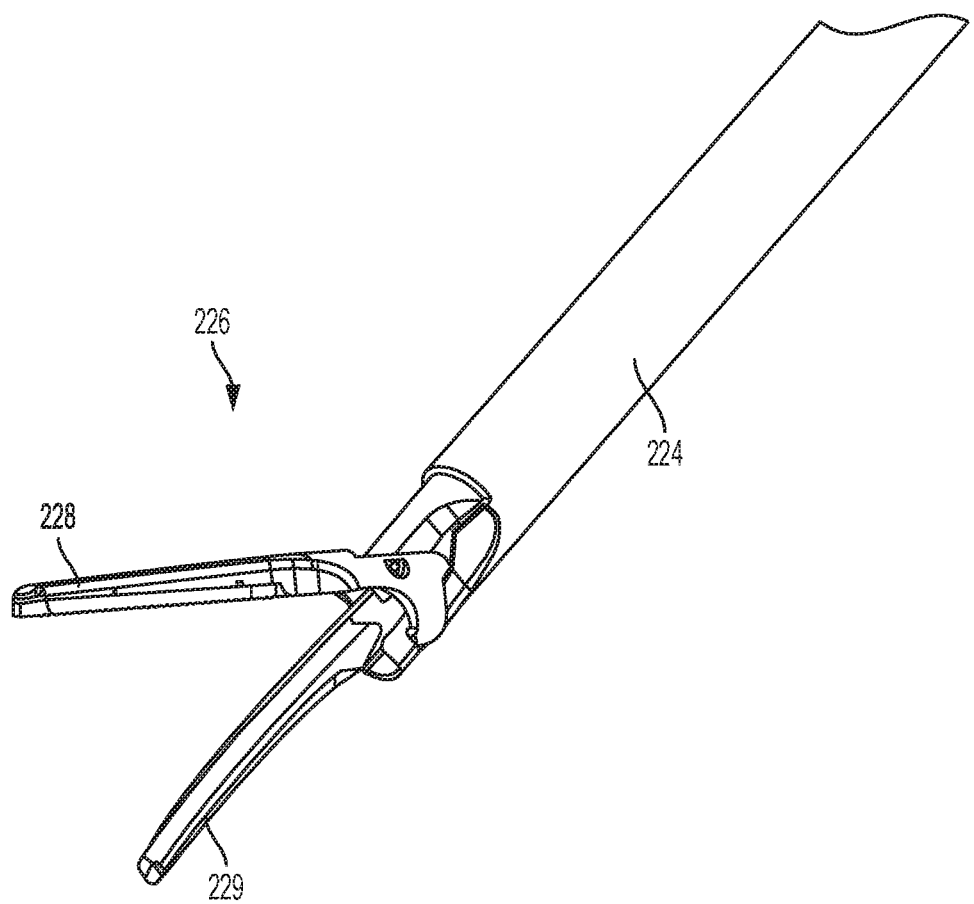
FIG. 4B is a side perspective view of a distal portion of the tool assembly of FIG. 4A, showing the end effector including a clamping arm relatively pivotally coupled to a blade.
Figure 4C:
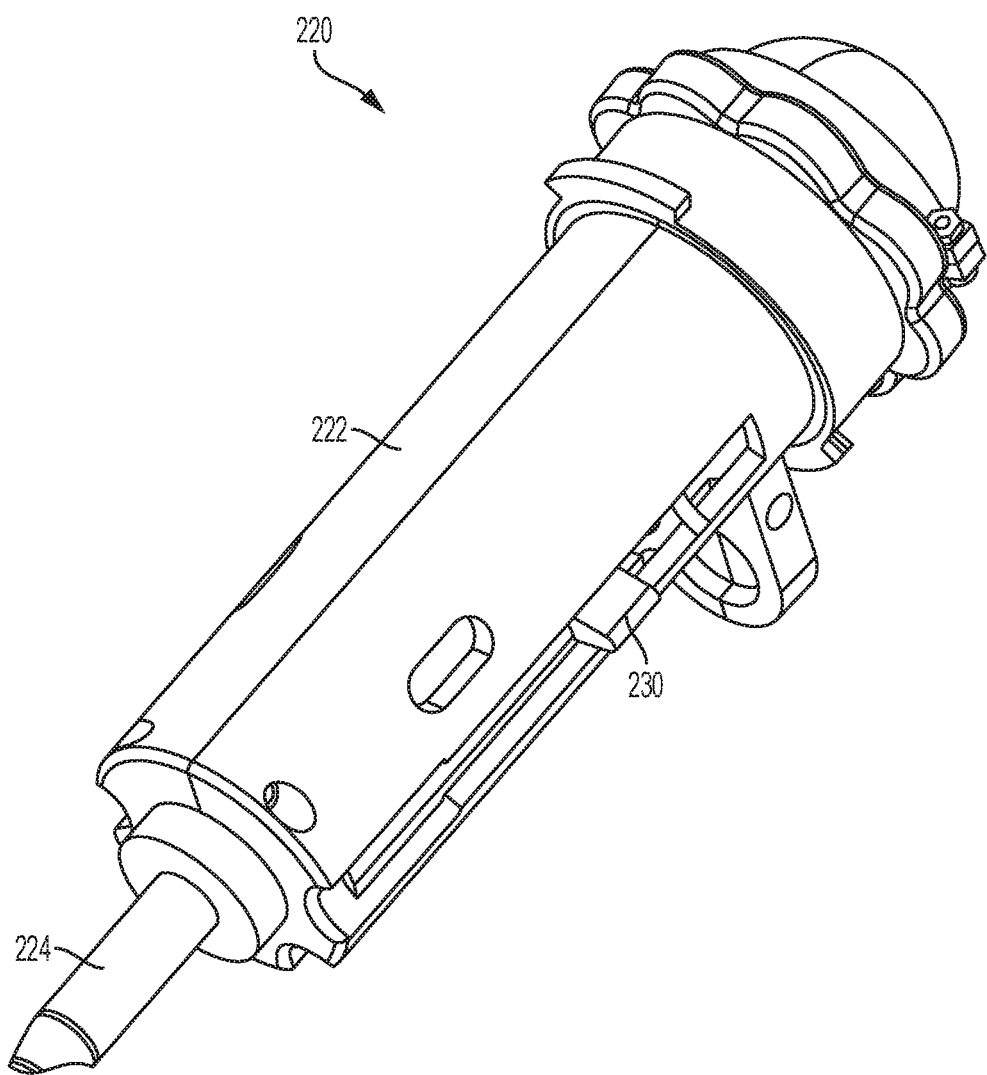
FIG. 4C is a side perspective view of a proximal portion of the housing of FIG. 4A, with at least one linear input coupling.
Figure 4D:
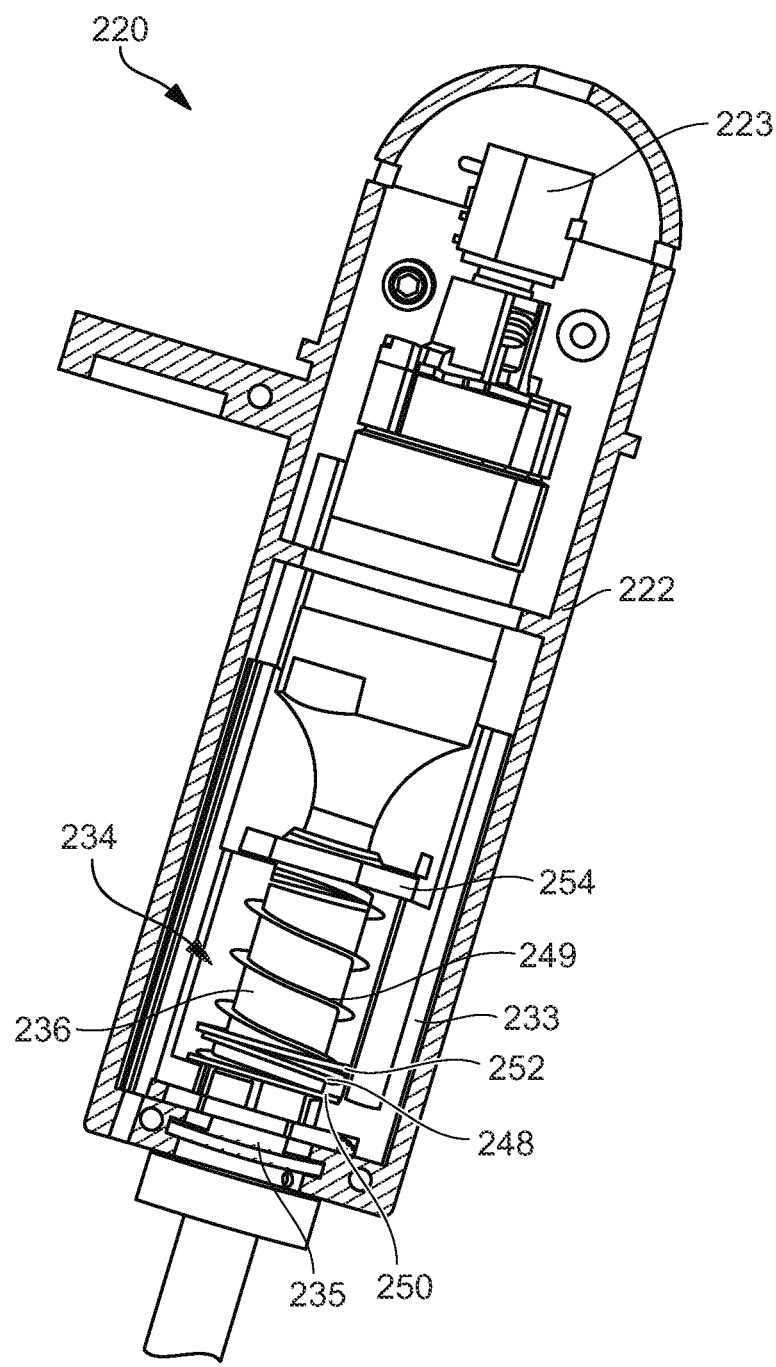
FIG. 4D is a side perspective cross-sectional view of the housing of FIG. 4A, with a yoke slidably disposed within the housing of the tool assembly.

FIGS. 4A-4E illustrate an exemplary embodiment of a tool assembly 220 having a housing 222 coupled to a proximal end of a shaft 224 and an end effector 226 coupled to a distal end of the shaft 224. The end effector 226 can include a clamp arm 228 that pivots relative to a blade 229. The clamp arm 228 can pivot between an open configuration where the clamp arm 228 and blade 229 are configured to receive tissue therebetween (see, for example, FIG. 4B) and a closed configuration where the clamp arm 228 and blade 229 are configured to either cut or seal tissue therebetween. The blade 229 can be ultrasonic and in communication with a transducer 223 that provides ultrasonic energy to the blade 229. For example, the housing 222 can include the transducer 223 (as shown in FIG. 4D) with a piezoelectric element that together generate a mechanical motion (e.g., vibration) at the blade 229. Movement of the clamp arm 228 to the closed configuration to compress tissue between the clamp arm 228 and blade 229 can improve the ability of the blade 223 to transfer ultrasonic energy to tissue for sealing and/or cutting tissue.

The housing 222 can include coupling features that assist with releasably coupling the housing 222 to the tool driver 112 of the robotic arm 108. For example, the housing 222 can include mechanisms that can be actuated by the one or more motors 114a-114d in the driver 112. As discussed above, any of the motors 114a-114d can be associated with a rotary or linear mechanical output (e.g., a rotating shaft or a linearly translating shaft), either of which can be configured to couple to a rotary input coupling or a linear input coupling on the tool assembly 110 for actuating at least one mechanism of the tool assembly 110. For example, as shown in FIG. 4C, an actuator, referred to as a linear input coupling 230, can project outward from the housing 222 and it can interact with a linear mechanical output of the tool driver 112 such that when the linear mechanical output is activated by one of the motors 114a-114d, the linear mechanical output can push on and translate the linear input coupling 230 thereby actuating a mechanism within the housing 222 for controlling one or more functions of the tool assembly 220. Such mechanism, for example, can control the operation of various features associated with the end effector 226 (e.g., pivoting of clamp arm 228 relative to blade 229, etc.), as will be described in greater detail below. In an exemplary embodiment, when the tool housing 222 is coupled to the tool driver 112, the tool driver 112 is positioned distal of the tool housing 222 such that the tool driver's mechanical outputs (e.g., linear and/or rotary mechanical outputs) are located at a proximal end of the tool driver 112. The mechanical outputs can interact with one or more inputs (e.g., the linear input coupling 230) located at the distal end of the tool housing 222. As a result of this configuration, proximal translation of a linear output on the tool driver 112 can act on and cause the tool's linear input coupling to travel proximally to active a mechanism within the tool housing 222. Furthermore, although the tool assembly 110 is described as having one linear input coupling 230, any of the tool assemblies described herein (including tool assembly 110) can include more than one rotary or linear input couplings that can be acted on by at least one output (e.g., manual, rotary and/or linear mechanical output) on a tool driver of a surgical robot for activating one or more mechanisms associated with the tool assembly. An exemplary embodiment of a tool driver having linear drivers is described in more detail in U.S. patent application Ser. No. 15/381,453 filed Dec. 16, 2016 and entitled "Methods and Systems for Coupling a Surgical Tool to a Tool Driver of a Robotic Surgical System," and U.S. patent application Ser. No. 15/381,508 filed Dec. 16, 2016 and entitled "Methods and Systems for Coupling a Surgical Tool to a Tool Driver of a Robotic Surgical System."

The shaft 224 can include drive assemblies extending along or through the shaft 224 for controlling the actuation and/or movement of the end effector 226 (e.g., pivoting of clamp arm 228 relative to blade 229). The end effector 226 can include any of a variety of surgical tools, such as the clamp arm 228 and blade 229, a stapler, a clip applier, forceps, a needle driver, a cautery device, a cutting tool, a pair of jaws, an imaging device (e.g., an endoscope or ultrasound probe), or a combined device that includes a combination of various tools. In the illustrated embodiment, the shaft 224 includes an inner closure tube 235 that extends therealong and that is slidably disposed relative to an outer closure tube 236 that is in fixed relation to the tool housing 222. A distal end of the inner closure tube 235 can be pivotally coupled to the clamp arm 228 such that proximal travel of the inner closure tube 235 causes the clamp arm 228 to pivot to the closed configuration and distal travel of the inner closure tube 235 causes the clamp arm 228 to pivot to the open configuration. Although the outer closure tube 236 is described as being in fixed relation relative to the tool housing 222 and the inner closure tube 235 is described as being slidably disposed relative to the outer closure tube 236, the inner closure tube 235 can be in fixed relation relative to the tool housing 222 and the outer closure tube 236 can be slidably disposed relative to the inner closure tube 235 without departing from the scope of this disclosure.

In one exemplary embodiment, as shown in FIG. 4D, the tool assembly 220 can include a yoke 233 that has an elongated tubular body that is slidably disposed within the housing. The yoke 233 can be coupled to or integral with the linear input coupling 230, and the yoke 233 can also couple to the inner closure tube 235. As a result, when the linear input coupling 230 is actuated and caused to move (e.g., via manually or by a linear mechanical output), the yoke 233 and inner closure tube 235 are caused to move thereby pivoting the clamp arm 228 between open and closed configurations. For example, when the linear input coupling 230 is actuated causing it to translate in a proximal direction, the yoke 233 and inner closure tube 235 can also be caused to translate in the proximal direction thereby pivoting the clamp arm 228 to the closed configuration. Deactivation or distal retraction of the linear output can allow or cause the yoke 233 and inner closure tube 235 to translate in a distal direction thereby pivoting the clamp arm 228 to the open configuration.

As shown in FIG. 4D, the tool assembly 220 includes a biasing system 234 that biases the yoke 233 in the distal direction and that biases the clamp arm 228 to the open configuration. For example, the biasing system 234 can bias the yoke 233 in a distal position, when there is no activation force (e.g., either manually or via a mechanical output) acting on the linear input coupling 230. As shown in FIG. 4D, the biasing system 234 can include a distal biasing member 248, such as a first spring, positioned between a distal compressing member 250 and a middle compressing member 252. The distal and middle compressing members 250, 252 can be, for example, washers and they can be slidably disposed along their respective inner openings along a proximal end of the outer closure tube 235, as shown in FIG. 4D. The yoke 233 can be rigidly coupled to the distal compressing member 250 such that proximal movement of the yoke 233 causes corresponding movement of the distal compressing member 250 in the proximal direction. The biasing system 234 can further include a proximal biasing member 249, such as a second spring, positioned between the middle compressing member 252 and a proximal compressing member 254. The distal, middle, and proximal compressing members 250, 252, 254 can be axially aligned (e.g., along a central axis) with each other, and can also be axially aligned with the distal and proximal biasing members 248, 249.

As noted above, the yoke 233 can be directly coupled to the distal compressing member 250 such that when the yoke 233 moves in the proximal direction (e.g., thereby pivoting the clamp arm 228 to the closed configuration), the distal compressing member 250 is moved in the proximal direction thereby compressing the distal biasing member 248 between the distal compressing member 250 and the middle compressing member 252. After the yoke 233 and distal compressing member 250 have moved a first distance thereby compressing the distal biasing member 248, the yoke 233 can continue to move in the proximal direction along with the distal compressing member 250, the distal biasing member 248, and the middle compressing member 252. As a result, the proximal biasing member 249 is compressed between the middle compressing member 252 and the proximal compressing member 254. In an exemplary embodiment, the distal biasing member 248 can have a first spring force that, when compressed, allows the clamp arm 228 to pivot into a closed or substantially closed configuration, and the proximal biasing member 249 can have a second spring force that, when compressed, allows the clamp arm 228 to apply compressive forces against tissue positioned between the clamp arm 228 and the blade 229. For example, the second spring force can be greater than the first spring force thereby allowing the clamp arm 228 to apply a greater force against tissue as the proximal biasing member is compressed compared to when the distal biasing member is compressed. The greater second spring force provided by the proximal biasing member can assist with allowing the blade 229 to seal and/or cut tissue positioned between the blade 229 and clamp arm 228. When manual or mechanical linear outputs are no longer applied to the linear input coupling 230, the distal and proximal biasing members 248, 249 can expand, thereby distally translating the middle and distal compressing members 252, 250, as well as the yoke 233 coupled to the distal compressing member 250, and pivoting the clamp arm 228 to the open configuration.

Figure 4E:
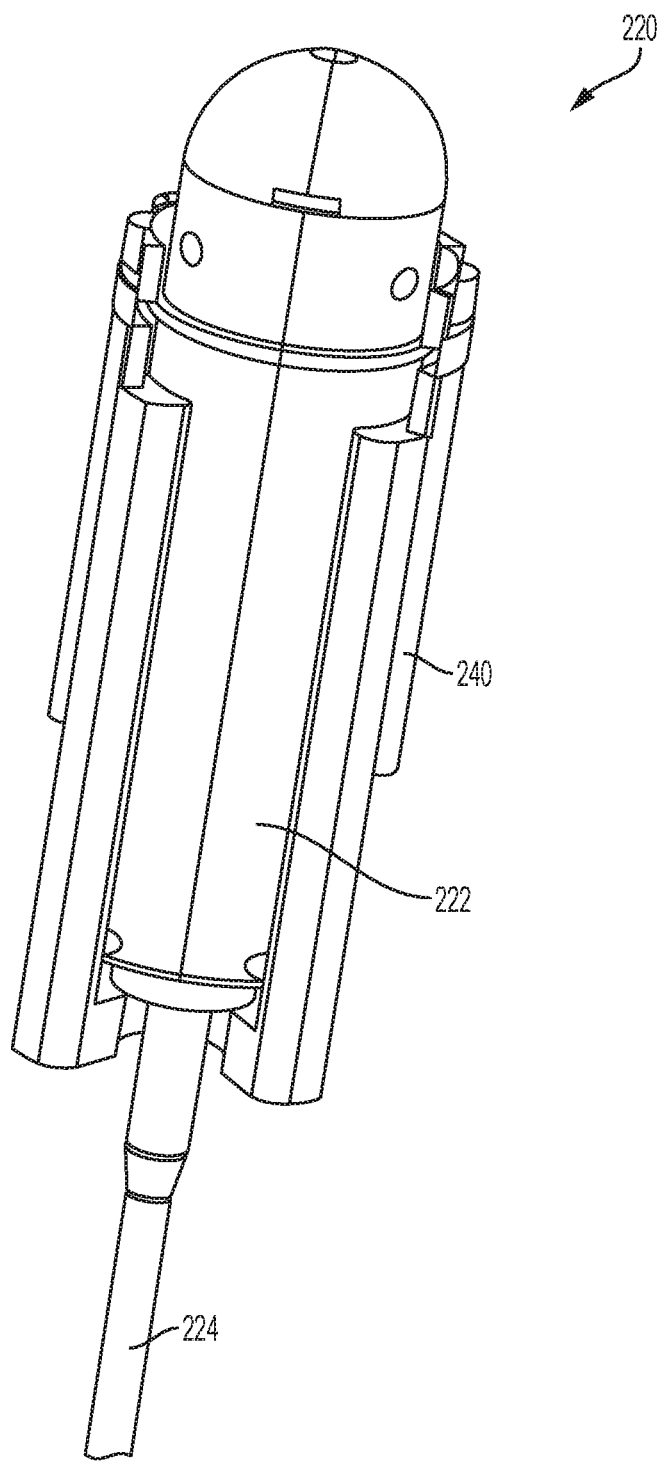
FIG. 4E is a side perspective view of a proximal portion of the housing of FIG. 4A, with a sterile barrier covering a portion of the housing.

FIG. 4E illustrates a sterile barrier 240 that can cover at least a portion of the outer surface of the housing 222 of the tool assembly 220. The sterile barrier 240 can be configured to provide a sterile barrier for the housing 222 while not interfering with coupling mechanisms that allow the tool assembly 220 to couple to the robotic arm 108, as well as not interfering with manual and/or mechanical inputs for actuating mechanisms associated with the tool assembly 220. For example, the sterile barrier 240 can allow the linear input coupling 230 to be acted upon by a linear mechanical output of the tool driver 112, as well as allow the linear input coupling 230 to translate thereby translating the yoke 233 to pivot the clamp arm 228. While not shown, a bag or drape can extend from the sterile barrier 240 to cover the robotic arm. A sterile component, such as an instrument sterile adapter (ISA) (not shown), can also be placed at the connecting interface between the tool assembly 110 and the robotic arm 108. The placement of an ISA between the tool assembly 110 and the robotic arm 108 can ensure a sterile coupling point for the tool assembly 110 and the robotic arm 108. This permits removal of tool assemblies 110 from the robotic arm 108 to exchange with other tool assemblies 110 during the course of a surgery without compromising the sterile surgical field.

Some embodiments of the tool assemblies disclosed herein can be configured to assist with tissue spread dissection using the clamp arm 228 and blade 229. As referred to herein, tissue spread dissection using the clamp arm 228 and blade 229 can include positioning the clamp arm 228 and blade 229 in a space between opposing tissue and pivoting the clamp arm 228 away from the blade 229 (from the closing configuration into an open configuration) thereby increasing the space between the opposing tissue. For example, such tissue spread dissection can be useful for passing objects through tissue, mobilization and/or viewing anatomy.

As discussed above, a biasing system 234 can cause the yoke 233 to translate in a distal direction once linear outputs are no longer acting on the linear input coupling 230, thus allowing the jaws to return to the open configuration. As such, the biasing system 234 can be configured such that it translates a force (e.g., tissue spread dissection force) through the yoke 233 and to the clamp arm 228 that is sufficient for allowing the clamp arm 228 to pivot to the open configuration thereby creating spread dissection to surrounding tissue. Due to the increased force requirements to spread tissue (compared to just pivoting the clamp arm 228 to an open configuration), the yoke 233 and/or associated mechanisms that assist with controlling the movement of the yoke (e.g., biasing system 234) can be configured to provide additional force to the clamp arm 228 for spreading tissue. Such additional force can be provided using currently available mechanical outputs, which may be less than the force requirements needed for tissue spread dissection. As such, some of the embodiments disclosed herein can include a mechanical advantage that, for example, increases the amount of force provided between the mechanical output and the clamp arm 228, as will be described in greater detail below.

For example, a spreading force applied to the opposing tissue for performing tissue spread dissection can require approximately 25 pounds of force to approximately 35 pounds of force. As such, biasing systems and/or or mechanical output mechanisms described herein that are operatively coupled to the clamp arm 228 can be configured to provide such required force for spread dissection. Furthermore, the biasing systems and/or or mechanical input mechanisms can be configured for providing more or less force without departing from the scope of this disclosure.

Figure 5:
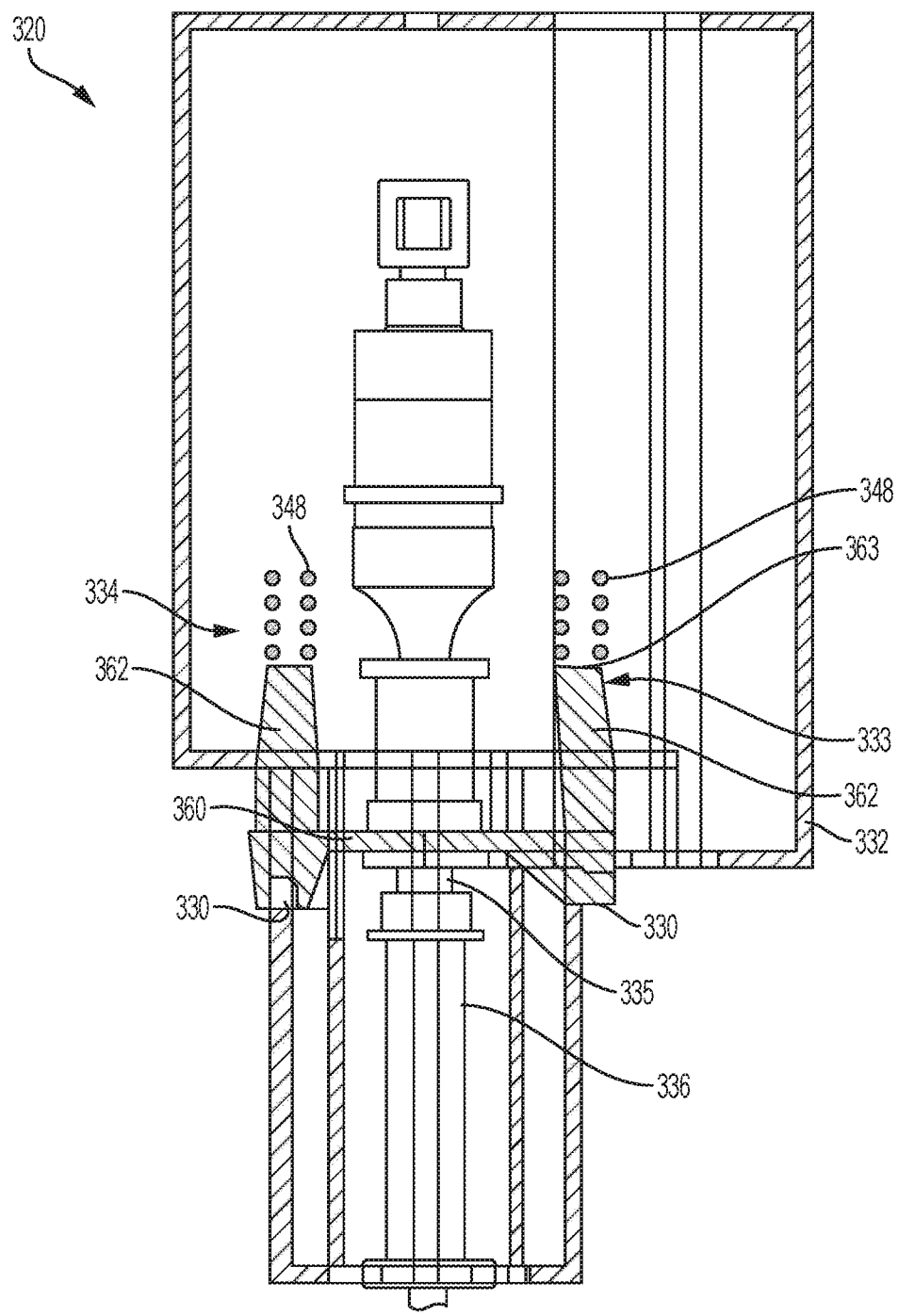
FIG. 5 is a partial cross-sectional view of another embodiment of a tool driver having a yoke coupled to two linear input couplings and a biasing system including a pair of springs.

FIG. 5 illustrates an embodiment of a tool assembly 320 including a yoke 333 coupled to a biasing system 334 that is configured to assist with tissue spread dissection, as will be described in greater detail below. As shown in FIG. 5, the yoke 333 can be positioned within and slidably disposed relative to the housing 322 of the tool assembly 320. The yoke 333 can be coupled to an inner closure tube 335 that extends along an outer tube 336 and shaft, with the inner tube 335 being operatively coupled to a clamp arm that can pivot relative to a blade (such as the clamp arm 228 and blade 229 of tool assembly 220). Similar to the embodiment described above with reference to tool assembly 220, when the yoke 333 is caused to translate, the inner closure tube 335 is caused to translate thereby causing the clamp arm to pivot between an open and closed configuration relative to the blade.

As shown in FIG. 5, the yoke 333 can include an extension 360 that couples to and extends between the inner closure tube 335 and a pair of yoke arms 362 that extend approximately parallel to a longitudinal axis of the inner closure tube 335. For example, the extension 360 can extend approximately perpendicular relative to the longitudinal axis of the inner closure tube 335. A distal end of each of the yoke arms 362 can include linear coupling inputs 330 that are configured to couple to linear mechanical outputs, such as from the tool driver 112. A proximal end of each of the yoke arms 362 can include a biasing coupling 363 (e.g., a flat surface) that is configured to couple to a biasing member 348 (e.g., spring). The biasing members 348 can compress when the linear input couplings 330 are each acted upon by a linear mechanical output thereby driving the yoke 333 in the proximal direction and pivoting the clamp arm to the closed position. When the linear mechanical outputs no longer apply a force against the yoke 333 (e.g., the linear mechanical outputs are deactivated), the biasing members 348 can each apply a biasing or spring force against the proximal end of the yoke 333 that together cause the yoke 333 to translate to the distal position thereby pivoting the clamp arm to the open configuration and spreading tissue. As such, the biasing system 334 can cause the clamp arm to pivot into the open configuration, including spreading tissue while pivoting into the open configuration, without a mechanical output, such as from the tool driver 112.

In some circumstances, manual control of the clamp arm can be desired, such as during loss of power and/or when the tool assembly 320 is disconnected from a robotic arm 108 and the clamp arm needs to be moved into the closed configuration in order to remove the end effector from the patient and trocar. The tool assembly 320 can thus include a manual controller (not shown) that can extend from the yoke 333 and through the housing 322 such that a user can manipulate the manual controller to move the yoke 333 between the distal and proximal positions thereby manually controlling the pivoting of the clamp arm between the open and closed configurations, respectively.

Figure 6:
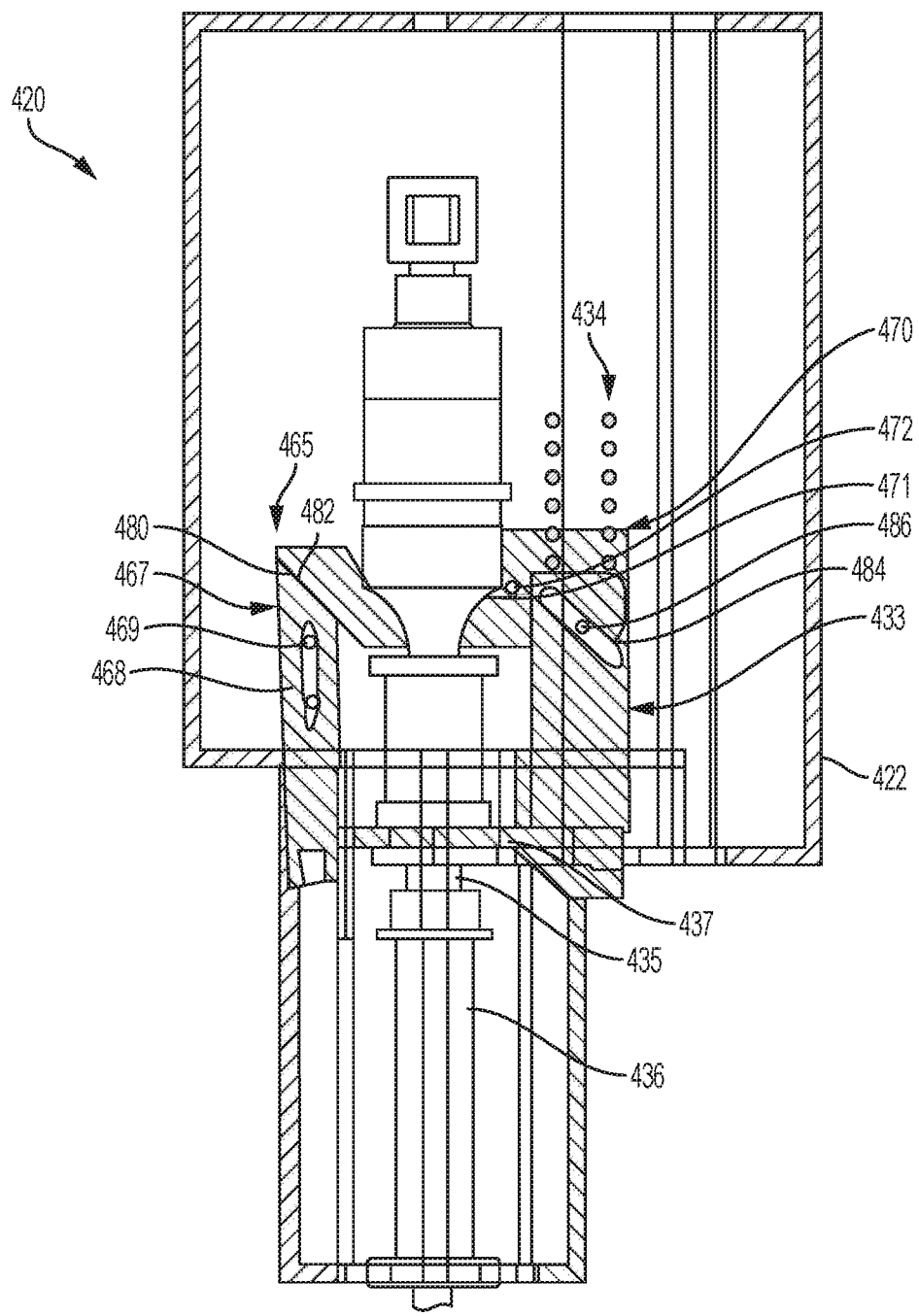
FIG. 6 is a partial cross-sectional view of yet another embodiment of a tool driver having a yoke coupled to a single linear input coupling and a biasing system including a single spring.

FIG. 6 illustrates another embodiment of a tool assembly 420 including a yoke 433 coupled to a biasing member or spring 434 positioned at a proximal end of the yoke for biasing the yoke 433 in the distal direction, thereby biasing the clamp arm to an open configuration. As shown in FIG. 6, the yoke 433 can include an elongated body that extends generally parallel to a housing 422 of the tool assembly 420. The yoke 433 can be slidably disposed within the housing 422 and coupled to an inner closure tube 435 by a closure tube coupling 437 that extends between the inner closure tube 435 and a distal end of the yoke 433. The inner closure tube 435 can slidably translate within an outer closure tube 436 that is fixed relative to the housing 422. Similar to the embodiment described above with reference to tool assembly 220, when the yoke 433 is caused to translate, the inner closure tube 435 translates relative to the outer closure tube 436 thereby causing a clamp arm to pivot between open and closed configurations relative to a blade.

As shown in FIG. 6, a proximal end of the yoke 433 can be slidably coupled to a linear input coupling assembly 465 that, when acted upon by a linear mechanical output, causes the yoke 433 to translate in a proximal direction thereby causing the clamp arm to pivot to a closed configuration. The linear input coupling assembly 465 can include a vertical sliding shaft 467 positioned parallel to the yoke 433 and the longitudinal axis of the inner closure tube 435. The vertical sliding shaft 467 can be constrained relative to the housing 422 such that the vertical sliding shaft 467 can only translate in a direction parallel to the longitudinal axis of the inner closure tube 435. As shown in FIG. 6, the vertical sliding shaft 467 can include a vertical slot 468 having a length that defines a maximum length of travel of the vertical sliding shaft 467. A first pin 469 can extend from the housing 422 into the slot 468 thereby controlling the travel of the vertical sliding shaft 467 to within the bounds of the vertical slot 468.

The linear input coupling assembly 465 can further include a horizontal sliding shaft 470 that extends perpendicular relative to the longitudinal axis of the inner closure tube 435, and that extends between the vertical sliding shaft 467 and the yoke 433, as shown in FIG. 6. The horizontal sliding shaft 470 can be constrained relative to the housing 422 such that the horizontal sliding shaft 470 can only slide in a direction perpendicular to the longitudinal axis of the inner closure tube 435. As shown in FIG. 6, the horizontal sliding shaft 470 can include a horizontal slot 471 having a length defining a maximum length of travel of the horizontal slot 471. A second pin 472 can extend from the housing 422 into the horizontal slot 471 thereby controlling the travel of the horizontal sliding shaft 470 to within the bounds of the horizontal slot 471.

A proximal end of the vertical sliding shaft 467 can include a first angled end 480 that slidably mates with a second angled end 482 of the horizontal sliding shaft 470. Such coupling allows the first angled end 480 to slide along the second angled end 482 and push the horizontal sliding shaft 470 towards the yoke 433 as the vertical sliding shaft 467 travels in the proximal direction (such as when the linear mechanical output is activated). This sliding coupling also allows the second angled end 482 to slide along the first angled end 480 and push the vertical sliding shaft 467 in the distal direction as the horizontal sliding shaft 470 travels towards the vertical sliding shaft 467 (such as when the linear mechanical output is deactivated).

Furthermore, a proximal end of the yoke 433 can include an angled slot 484 and the horizontal sliding shaft 470 can include a yoke pin 486 at an end adjacent the yoke 433. The yoke pin 486 can extend into and be slidable along the angled slot 484 such that when the horizontal sliding shaft 470 travels perpendicular to the longitudinal axis of the inner closure tube 435, the yoke 433 is caused to travel parallel to the longitudinal axis of the inner closure tube 435. For example, when the horizontal sliding shaft 470 travels towards the yoke 433, the yoke 433 is caused to move in the proximal direction thereby compressing the biasing member 434 and pivoting the clamp arm into the closed configuration. In this configuration, the angled coupling between the horizontal sliding shaft 470 and the yoke 433 can desensitize the effects of the mechanical linear output relative to the pivoting of the clamp arm. For example, the vertical sliding arm 467 can travel a first distance that results in the yoke 433 traveling half of the first distance thereby pivoting the clamp arm a smaller distance compared to the yoke having a 1:1 travel ratio with the vertical sliding shaft 467 and/or mechanical liner output. The angled couplings of the linear input coupling assembly 465 can also provide a mechanical advantage such that the mechanical output force can be less than the spring force of the biasing member 434 yet the linear input coupling assembly 465 can act upon the yoke 433 to compress the biasing member 434. For example, the biasing member 434 can have sufficient spring force to drive the yoke 433 in the distal direction to pivot the clamp arm for performing tissue spread dissection.

In some implementations, the linear input coupling assembly 465 can be configured to allow more than one linear mechanical output to apply a force against the linear input coupling assembly 465, such as the vertical sliding shaft 467, for activating the linear input coupling assembly 465 and translating the yoke 433. Any number of mechanical outputs can activate the linear input coupling assembly 465 for causing the yoke to translate in the proximal direction thereby pivoting the clamp arm to the closed configuration.

In some embodiments, the tool assembly 420 can include a manual controller (not shown) that can extend from the yoke 433 and through the housing 422 such that a user can manipulate the manual controller to move the yoke 433 between the distal and proximal positions thereby manually controlling the pivoting of the clamp arm between the open and closed configurations. For example, manual control of the clamp arm can be desired, such as during loss of power and/or when the tool assembly is disconnected from a robotic arm and the clamp arm needs to be moved into the closed configuration in order to remove the end effector from the patient and trocar.

In some implementations of the tool assembly, the linear mechanical output can control bi-directional movement of the yoke, such as proximal and distal translation of the yoke relative to the housing of the tool assembly to cause the clamp arm to pivot between closed and open configurations, respectively. In such configurations, for example, the mechanical output (e.g., from a tool driver) can assist with tissue spread dissection.

Figure 7A:
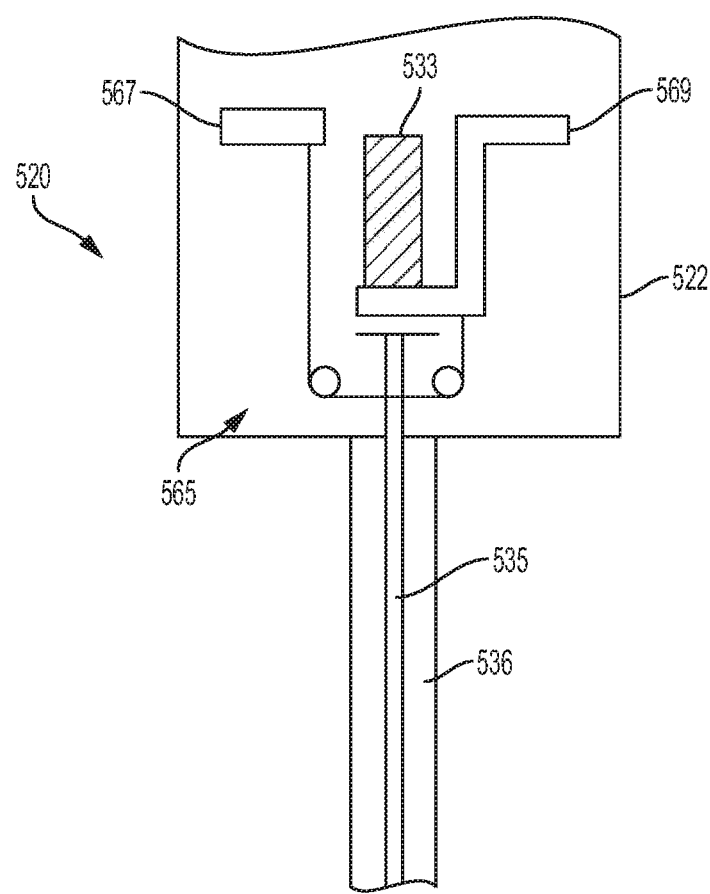
FIG. 7A is a side perspective view of another embodiment of a yoke controlled by two linear actuators.

FIG. 7A illustrates another embodiment of a tool assembly 520 that includes a yoke 533 that can have bi-directional movement (e.g., proximal and distal directed translation) controlled by mechanical linear outputs. As shown in FIG. 7A, the yoke 533 can include an elongated body that extends generally parallel to a housing 522 of the tool assembly 520. The yoke 533 can be positioned within and slidably disposed relative to a housing 522. The yoke 533 can be coupled to an inner closure tube 535 such that when the yoke 533 is caused to translate between a distal and proximal position, the inner closure tube 535 is caused to translate thereby causing a clamp arm at a distal end of the inner closure tube 535 to pivot between open and closed configurations, respectively, relative to a blade. The inner closure tube 535 can extend along and be slidably disposed relative to an outer closure tube 536 that is fixed relative to the housing 522.

As shown in FIG. 7A, the yoke 533 can be coupled to an actuation assembly 565 that includes an opening actuator 567 and a closing actuator 569 that are each configured to couple to a linear mechanical output for individually translating the opening and closing actuators 567, 569 in a proximal direction. The actuation assembly 565 can further include a pulley system 570, which can include one or more pulleys that connect the closing actuator 569 to the opening actuator 567. For example, the closing actuator 569 can be directly coupled to the yoke 533, as shown in FIG. 7A. The pulley system 570 can be configured such that when the closing actuator 569 is caused to move in the proximal direction (thereby translating the yoke 533 in the proximal direction and pivoting the clamp arm to the closed configuration) the opening actuator 567 is caused to move distally. Furthermore, the pulley system 570 can be configured such that when the opening actuator 567 is caused to move in the proximal direction, the closing actuator 569 is caused to move in the distal direction thereby moving the yoke 533 distally and pivoting the clamp arm to the open configuration.

Figure 7B:
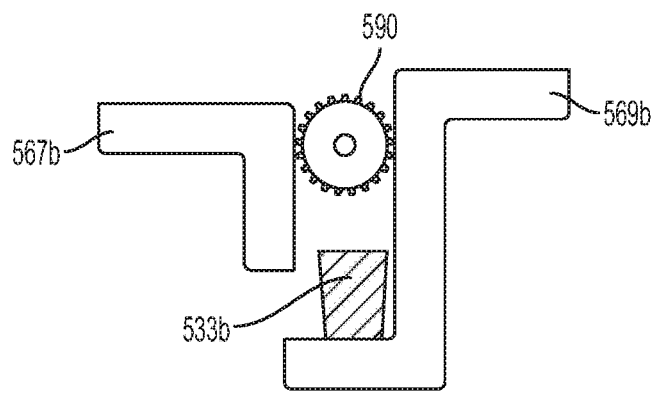
FIG. 7B is a side perspective view of yet another embodiment of a yoke controlled by two linear actuators.

As shown in FIG. 7B, instead of the pulley system 570, a pinion gear 590 can couple a closing actuator 569b to an opening actuator 567b. For example, the closing actuator 569b can be directly coupled to the yoke 533b, as shown in FIG. 7B. The pinion gear 590 can be engaged with the closing actuator 569b along a first side of the pinion gear 590 and engaged with the opening actuator 567b along a second side (e.g., opposite the first side) of the pinion gear 590 such that when the closing actuator is caused to move in the proximal direction (thereby translating the yoke 533b in the proximal direction and pivoting the clamp arm to the closed configuration) the opening actuator 567b is caused to move distally. Furthermore, when the opening actuator 567b is caused to move in the proximal direction, the pinion gear 590 can cause the closing actuator 569b to move in the distal direction thereby moving the yoke 533b distally and pivoting the clamp arm to the open configuration. Other mechanisms for coupling the opening actuator and closing actuator, such as a pivoted linkage, have been contemplated and are within the scope of this disclosure.

Figure 8:
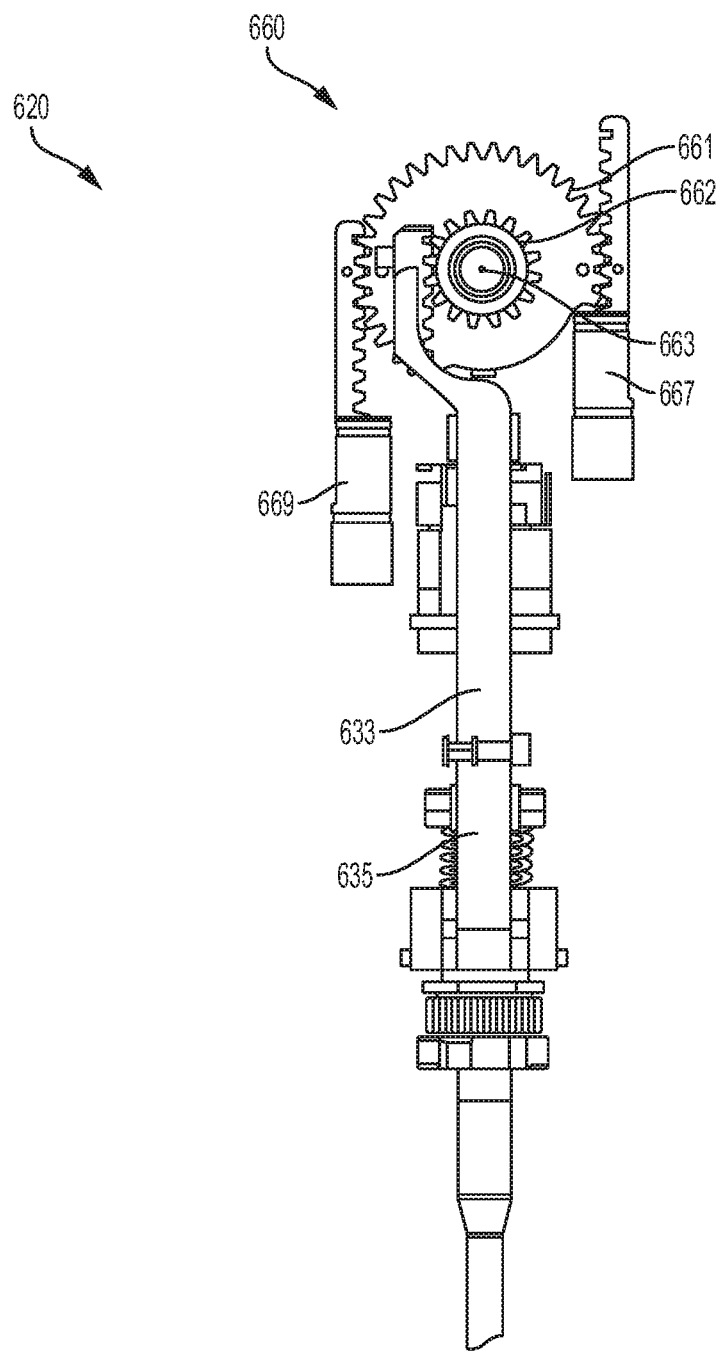
FIG. 8 is a side perspective view of another embodiment of a yoke and biasing system including a compound gear.

FIG. 8 illustrates yet another embodiment of a tool assembly 620 that includes a yoke 633 that can also have bi-directional movement (e.g., proximal and distal directed movement) controlled by mechanical linear outputs. The yoke 633 can include an elongated body that extends generally parallel to a housing of the tool assembly 620. The yoke 633 can be positioned within and slidably disposed relative to a housing. The yoke 633 can be coupled to an inner closure tube 635 such that when the yoke 633 is caused to translate, the inner closure tube 635 is caused to translate thereby pivoting a clamp arm open and closed configurations relative to a blade.

As shown in FIG. 8, the yoke 633 can be coupled to an actuation assembly 665 that includes an opening actuator 667 and a closing actuator 669 that are each configured to couple to a linear mechanical output for individually translating the opening and closing actuators 667, 669 in a proximal direction. The actuation assembly 665 can further include a compound gear 660 that mechanically couples the closing actuator 669 to the opening actuator 667. Furthermore, the compound gear 660 can mechanically couple the opening and closing actuators 667, 669 to the yoke 633 such that translational movement of either the opening or closing actuators 667, 669 cause translation of the yoke 633.

For example, the compound gear 660 can include a first gear 661 and a second gear 662 that share a pivot point or rotational axis 663 and are affixed relative to each other such that they are forced to rotate together. Furthermore, the second gear 662 can have a smaller diameter than the first gear 661, as shown in FIG. 8. For example, the diameter of the second gear 662 can be half of the diameter of the first gear 661, thereby allowing the compound gear 660 to have a 2:1 mechanical advantage between the smaller second gear 662 and the larger first gear 661. The larger first gear 661 can be coupled to the opening and closing actuators 667, 669 that are each positioned and engaged along opposing sides of the first gear 661, as shown in FIG. 8. The opening and closing actuators 667, 669 can be engaged with the first gear 661 such that linear translation of both the opening and closing actuators 667, 669 in opposite directions (e.g., opening actuator 667 translates in distal direction and closing actuator 669 translates in proximal direction) causes the first gear 661 to rotate. The smaller second gear 662 can be coupled to the yoke 633 such that rotation of the second gear 662 causes the yoke 633 to linearly translate. As such, linear movement of the opening and closing actuators 667, 669 can cause rotation of the first and second gears 661, 662 thereby translating the yoke 633 and causing the clamp arm 628 to pivot. Furthermore, as a first torque is applied to the larger first gear 661, an output second torque (e.g., via the clamp arm) from the smaller second gear 662 can be greater than the first torque, such as twice as much. Likewise, a first arc length resulting from rotation of the larger first gear 661 can be greater than a second arc length resulting from the associated rotation of the smaller second gear 662, such as twice as much. The compound gear can provide a mechanical advantage such that more force is provided to the clamp arm for spread dissection than the amount of force applied to the first gear from the linear mechanical output. The compound gear can also provide desensitization between the mechanical linear actuator(s) and the yoke 633 (and clamp arm) by having the yoke 633 translate at a slower rate than the opening and closing actuators 667, 669 thereby allowing for improved precision and control of the yoke 633 and clamp arm.

Figure 9:
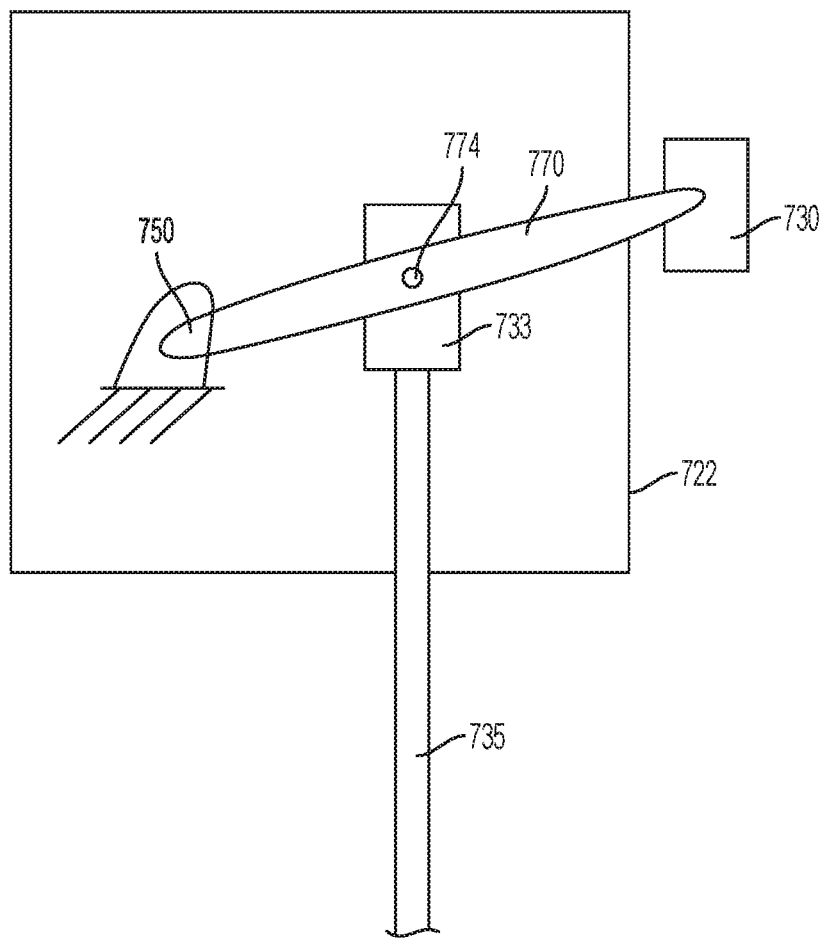
FIG. 9 is a side perspective view of another embodiment of a yoke and biasing system including a lever arm.

FIG. 9 illustrates yet another embodiment of a tool assembly 720 that includes a yoke 733 that can also have bi-directional movement (e.g., proximal and distal directed movement) controlled by mechanical linear outputs. The yoke 733 can include an elongated body that extends generally parallel to a housing 722 of the tool assembly 720. The yoke 733 can be positioned within and slidably disposed relative to the housing 722. The yoke 733 can be coupled to an inner closure tube 735 such that when the yoke 733 is caused to translate, the inner closure tube 735 is caused to translate thereby pivoting a clamp arm between open and closed configurations relative to a blade.

As shown in FIG. 9, the yoke 733 can be coupled to a lever arm 770. The lever arm 770 can be coupled to a pivot joint 750 at a first end. In some embodiments, the pivot joint 750 can be affixed to the housing 722. The lever arm 770 can be coupled to or interface with an actuator or linear input coupling 730 at a second end of the lever arm 770. At some point between the two ends of the lever arm 770, the lever arm 770 can be pivotally coupled to the yoke 733 at a lever coupling 774, as shown in FIG. 9. This configuration can provide a mechanical advantage, such as the mechanical output (via linear input coupling 730) to yoke 733 having approximately a 2:1 travel ratio. For example, a travel distance of the linear input coupling 730 (e.g., when acted upon by a linear mechanical output) can be twice as long as the resulting distance the yoke 733 travels. Furthermore, this configuration can provide a 1:2 force mechanical advantage where the force applied by the mechanical linear output can be half as much as the force applied to the yoke 733 by the lever arm 770.

Although the embodiments described above discuss linear mechanical outputs for controlling the movement of the yoke for pivoting the clamp arm, some implementations of the tool assembly can include a yoke that is controlled by at least one mechanical rotary output, as will be described in greater detail below.

Figure 10:
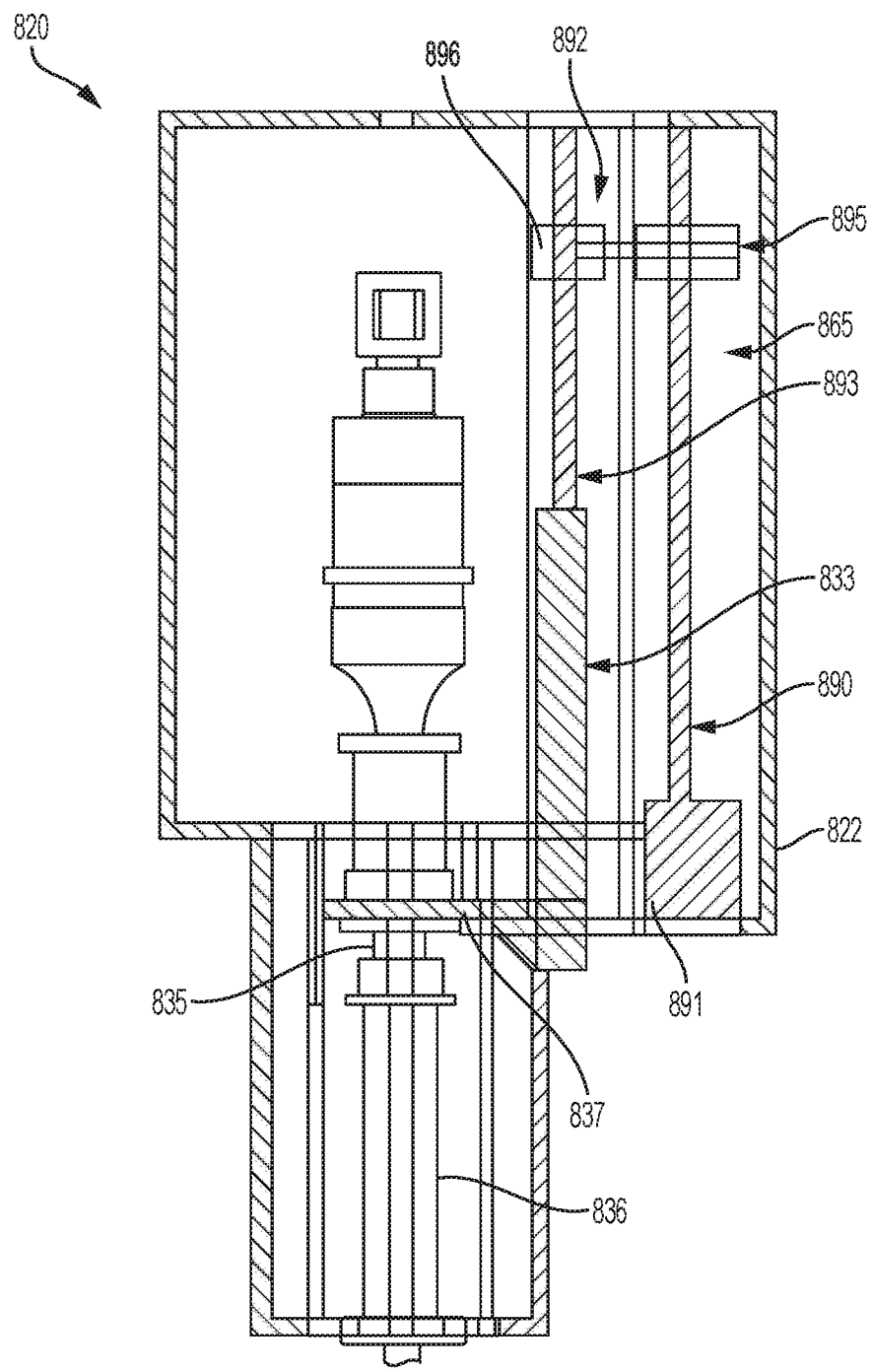
FIG. 10 is a partial cross-sectional view of yet another embodiment of a tool driver having a yoke and biasing member controlled by a rotary output.

FIG. 10 illustrates an embodiment of a tool assembly 820 having a yoke 833 coupled to a actuation assembly 865 that is controlled by at least one mechanical rotary output on a tool driver of a surgical robot. As shown in FIG. 10, the yoke 833 can include an elongated body that extends generally parallel to a housing 822 of the tool assembly 820. The yoke 833 can be slidably disposed within the housing 822 and coupled to an inner closure tube 835 by a closure tube coupling 837 that extends between the inner closure tube 835 and a distal end of the yoke 833. The inner closure tube 835 can slidably translate within an outer closure tube 836 that is fixed relative to the housing 822. When the yoke 833 is caused to translate, the inner closure tube 835 translates relative to the outer closure tube 836 thereby causing a clamp arm to pivot between open and closed configurations relative to a blade.

As shown in FIG. 10, the actuation assembly 865 can include an axillary shaft 890 that has a rotary input coupling 891 at a distal end that is configured to couple to a mechanical rotary output such that when the mechanical rotary output is activated the auxiliary shaft 890 is caused to rotate. The actuation assembly 865 can further include a pulley assembly 892 that can couple to and extend between the auxiliary shaft 890 and a lead screw 893. As shown in FIG. 10, the lead screw 893 can extend from the yoke 833, such as from a proximal end, and can be threadably coupled to the yoke 833 such that rotation of the lead screw 893 causes the yoke 833 to translate. For example, when the lead screw 893 rotates in a first direction, the yoke 833 travels in a proximal direction (e.g., clamp arm pivots to closed configuration) and when the lead screw 893 rotates in a second direction, the yoke 833 travels in a distal direction (e.g., clamp arm pivots to open configuration). The pulley assembly 892 can include a first pulley 895 and a second pulley 896 with the first pulley 895 being coupled to the auxiliary shaft 890 and the second pulley 896 being coupled to the lead screw 893 such that rotation of the auxiliary shaft 890 causes the first pulley 895 to rotate and transmit a torque to the second pulley 896 thereby causing the lead screw 893 to rotate.

In some circumstances, manual control of the clamp arm can be desired, such as during loss of power and/or when the tool assembly is disconnected from a robotic arm and the clamp arm needs to be moved into the closed configuration in order to remove the end effector from the patient and trocar. For example, the tool assembly 820 can include a manual controller (not shown), such as a lever, button, or latch, that can extend from the yoke 833 and through the housing 822 such that a user can manipulate the manual controller to move the yoke 833 between the distal and proximal positions thereby manually controlling the pivoting the clamp arm between the open and closed configurations, respectively. Furthermore, the yoke can include a split nut (not shown) such that actuation of the manual controller can spread apart the split nut thereby uncoupling the yoke 833 to the lead screw 893. To reset the yoke 833 and lead screw 893 coupling, such as in preparation to couple the tool assembly to a robotic arm, the split nut can be reengaged. A secondary process step may be necessary following such manual control in order to allow the control unit to determine the position of the yoke 833, such as relative to the lead screw 893. Such secondary process step can be performed, for example, after coupling the tool assembly to the robotic arm.

Any of the tool assemblies described herein can include various power switch mechanisms that control the delivery of power to the tool assemblies. Such power switch mechanisms can provide a safety feature to ensure persons handling the tool assemblies do not get electrocuted. For example, a surgeon can perform a surgical procedure with the tool assembly and at some point hand the tool assembly to a nurse, such as to allow the nurse to clean a part of the tool assembly. The power switch mechanism can ensure that power is appropriately shut off within the tool assembly to ensure the nurse does not get electrocuted while cleaning the tool assembly.

For example, in some embodiments, the power switch mechanisms can be in communication with a generator, a foot switch, and a hand activation such that which ever one is activated first, that one gets priority and the others are either turned off or ignored. In some embodiments, the power switch mechanisms can include a manual control that a user can select via a toggle between surgeon controls or bedside control. For example, the toggle can be on the generator. In some embodiments, the power switch mechanisms can include a toggle on the tool assembly that allows the bedside user to take control of the tool assembly. In some embodiments, the power switch mechanisms can include an active selection, e.g., a menu, button or switch on a console, etc. In some embodiments, the power switch mechanisms can include automatic control via a docking switch on the tool assembly that knows when it is docked to the robotic arm and when it is not. For example, when the tool assembly is mounted to the robotic arm, the user or surgeon can have control. When the tool assembly is removed from the robotic arm, hand activation can become active and the user or surgeon can lose control of the tool assembly.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:
1. A method for clamping tissue, comprising:
actuating a motor on a driver tool of a surgical robot to cause the motor to apply a force to first and second actuators on a surgical tool, linear movement of the first actuator causing longitudinal translation of a yoke disposed within a housing of the surgical tool in a first direction about a shaft assembly extending through the housing so as to move a clamp arm on an end effector of the surgical tool from an open position to a closed position to thereby engage tissue between the clamp arm and a blade, and linear movement of the second actuator causing longitudinal translation of the yoke in a second direction that is opposite from the first direction so as to move a clamp arm from the closed position to the open position.

2. The method of claim 1, wherein proximal translation of the yoke compresses a biasing member that biases the yoke distally.

3. The method of claim 1, wherein the motor applies one of a linear force and a rotational force to the actuator to cause the yoke to translate linearly.

4. The method of claim 1, wherein movement of the yoke a first distance causes the clamp arm to apply a first force against the tissue engaged between the clamp arm and the blade, and further movement of the yoke a second distance causes the clamp arm to apply a second force against the tissue engaged between the clamp arm and the blade, the second force being greater than the first force.

5. A method for clamping tissue, comprising:
   actuating a motor on a driver tool of a surgical robot to cause the motor to apply a force to at least one linear actuator projecting outward from a at least one slot in a housing of a surgical tool, the force causing longitudinal translation of the at least one linear actuator along the slot to thereby cause longitudinal translation of a yoke coupled to the at least one linear actuator and disposed within the housing about a shaft assembly extending through the housing so as to move a clamp arm on an end effector of the surgical tool between open and closed positions to thereby engage tissue between the clamp arm and a blade; and
   manually grasping the at least one linear actuator on the surgical tool to move the at least one linear actuator longitudinally along the slot to thereby move the yoke about the shaft assembly so as to move the clamp arm on the end effector between the open and closed positions.

6. The method of claim 5, wherein the at least one linear actuator comprises first and second linear actuators, and wherein movement of the first linear actuator in a first direction causes the clamp arm to move from the open position to the closed position, and movement of the second linear actuator in a second direction opposite the first direction causes the clamp arm to move from the closed position to the open position.

7. The method of claim 5, wherein proximal translation of the yoke compresses a biasing member that biases the yoke distally.

8. The method of claim 5, wherein the motor applies one of a linear force and a rotational force to the at least one actuator to cause the yoke to translate longitudinally.

9. The method of claim 5, wherein movement of the yoke a first distance causes the clamp arm to apply a first force against tissue engaged between the clamp arm and the blade, and further movement of the yoke a second distance causes the clamp arm to apply a second force against the tissue engaged between the clamp arm and the blade, the second force being greater than the first force.

* * * * *